(12) United States Patent
Dougherty et al.

(10) Patent No.: US 10,548,588 B2
(45) Date of Patent: *Feb. 4, 2020

(54) SUTURE-ANCHORING IMPLANTED MEDICAL DEVICES ENGINEERED FROM BIORESORBABLE METAL ALLOYS

(71) Applicant: Tenjin LLC, Brazoria, TX (US)

(72) Inventors: Christopher P. Dougherty, Rogers, AR (US); Gary R. Heisler, Brazoria, TX (US); Robert A. Van Wyk, St. Pete Beach, FL (US)

(73) Assignee: Tenjin LLC, Brazoria, TX (US)

( * ) Notice: Subject to any disclaimer, the term of this patent is extended or adjusted under 35 U.S.C. 154(b) by 272 days.

This patent is subject to a terminal disclaimer.

(21) Appl. No.: 15/463,415

(22) Filed: Mar. 20, 2017

(65) Prior Publication Data

US 2017/0189009 A1    Jul. 6, 2017

Related U.S. Application Data

(63) Continuation of application No. 14/817,061, filed on Aug. 3, 2015, now Pat. No. 9,597,069.

(60) Provisional application No. 61/999,648, filed on Aug. 2, 2014.

(51) Int. Cl.
*A61B 17/04* (2006.01)
*A61F 2/08* (2006.01)
*A61B 17/00* (2006.01)

(52) U.S. Cl.
CPC ........ *A61B 17/0401* (2013.01); *A61F 2/0811* (2013.01); *A61B 2017/00004* (2013.01); *A61B 2017/044* (2013.01); *A61B 2017/0445* (2013.01); *A61B 2017/0448* (2013.01); *A61B 2017/0458* (2013.01); *A61F 2002/0817* (2013.01); *A61F 2002/0841* (2013.01); *A61F 2002/0858* (2013.01); *A61F 2210/0004* (2013.01)

(58) Field of Classification Search
CPC ..... A61B 2017/0414; A61B 2017/0412; A61F 2002/0888; A61F 2002/0858; A61F 2002/0882; A61F 2002/0829
See application file for complete search history.

(56) References Cited

U.S. PATENT DOCUMENTS

| 8,246,762 B2 | 8/2012 | Janko et al. |
| 8,591,672 B2 | 11/2013 | Janko et al. |
| 9,226,817 B2 | 1/2016 | Dougherty et al. |
| 9,566,060 B2 | 2/2017 | Dougherty et al. |
| 9,597,069 B2 | 3/2017 | Dougherty et al. |
| 2010/0049259 A1* | 2/2010 | Lambrecht ............. A61F 2/442 606/86 R |
| 2010/0174367 A1* | 7/2010 | Janko .................... A61L 31/022 623/11.11 |

(Continued)

*Primary Examiner* — Katherine M Shi
(74) *Attorney, Agent, or Firm* — Chalin A. Smith; Smith Patent, LLC

(57) ABSTRACT

Herein described are suture-anchoring implanted medical devices formed from a bioresorbable metal alloy that may be used to secure soft tissue to bone. The metallic bioresorbable tissue anchoring devices of the present invention are optimally configured such that all portions of the device are resorbed over a short predetermined period of time while maintaining their tissue anchoring capability and preventing the generation of loose foreign bodies therefrom.

17 Claims, 8 Drawing Sheets

(56) References Cited

U.S. PATENT DOCUMENTS

2016/0100630 A1  4/2016  Clark et al.

* cited by examiner

SUTURE-ANCHORING IMPLANTED MEDICAL DEVICES ENGINEERED FROM BIORESORBABLE METAL ALLOYS

PRIORITY

This application is a continuation of U.S. application Ser. No. 14/817,061 filed Aug. 3, 2015, which issued as U.S. Pat. No. 9,597,069 on Mar. 21, 2017 and which, in turn, claims the benefit of U.S. Provisional Application Ser. No. 61/999,648 filed Aug. 2, 2014, the entire contents of which are hereby incorporated by reference.

TECHNICAL FIELD OF THE INVENTION

The present invention relates generally to the field of endoscopic and arthroscopic surgery and implant devices for use therein. More particularly, the invention relates to suture anchoring medical implant devices formed from a bioresorbable metal alloy that are used to secure soft tissue to bone. Specifically, the invention relates to metallic bioresorbable tissue anchoring implantable devices configured such that all portions of the implant resorb over a short predetermined period of time while maintaining their tissue anchoring capability and preventing the generation of loose bodies therefrom.

BACKGROUND OF THE INVENTION

The use of implants to affix tissue grafts to bone is well known in the orthopedic arts. Common procedures in which such implants are used include, for example, the repair of rotator cuff tears, the repair of torn ligaments in the knee, among others. When using a first type of anchoring implant, the implant (commonly referred to as an "anchor" or "suture anchor") is placed in a socket prepared in the surface of a target bone and the target tissue (also referred to as a "graft") is secured to the bone by sutures passing through the anchor. A second type of anchoring implant commonly referred to as an "interference screw" secures tissue to bone by trapping it between the implant and the wall of a socket formed in the bone. In either context, the socket is generally formed by drilling or punching at a predetermined location. The graft, generally a tendon or ligament, is inserted into the socket and the interference screw is threaded into the socket thereby securing tissue trapped between the implant and the wall of the socket. Implants of both types may be formed from metallic materials, polymers, or bioabsorbable materials. Metallic anchors have a high pull-out strength, but remain in the body of the patient indefinitely. On the other hand, bioabsorbable materials degrade in the body, but the reduced strength of the materials necessitate designs having thicker cross-sections which, in turn, limits the sizes and configurations in which these anchors can be produced.

Janko, et al. in U.S. Pat. Nos. 8,591,672 and 8,246,762 describe ". . . medical devices comprising high-strength alloys which degrade over time in the body of a human or animal, at controlled degradation rates, without generating emboli." See Abstract of Janko '672. The Janko invention is intended to provide "implantable medical devices comprising a biodegradable alloy that dissolves gradually from its exterior surface" wherein, in certain embodiments, "the rate of dissolution from the exterior surface of the alloy is substantially uniform across smooth portions of the exterior surface." See Janko '672, col. 2, lines 26-31. Janko recites a number of devices that may advantageously be formed from these materials. Quoting Janko '672, at col. 3, lines 45-52: "In certain embodiments, the implantable medical device is a high tensile bone anchor (e.g., for the repair of separated bone segments). In other embodiments, the implantable medical device is a high tensile bone screw for fastening fractured bone segments). In other embodiments, the implantable medical device is a high strength bone immobilization device (e.g., for large bones). In other embodiments, the implantable medical device is a staple for fastening tissue." Further quoting Janko '672, from col. 15, lines 5-17: "A substantially cylindrical device, which would lose surface area linearly with the loss of diameter as the device degrades, could have a concentric hole drilled through the center of the device. The resulting cavity would cause a compensating increase in surface area as alloy was dissolved from the luminal surface of the device. As a result, the change in surface area as the device degrades over time and thus the change in rate of degradation would be minimized or eliminated. A similar strategy of creating a luminal space (e.g., a luminal space that has a shape similar to the outer surface of the device) could be implemented with essentially any type of medical device."

The techniques for increasing the ratio of surface area to volume taught by Janko are readily applied to fasteners of cylindrical geometry, such as screws. However, contrary to Janko's suggestion that "a luminal space that has a shape similar to the outer surface of the device) could be implemented with essentially any type of medical device", it is in fact not possible to produce a luminal space in conventional metal suture anchors currently available for affixing soft tissue to bone, examples of which include the Revo Suture Anchor by Conmed, Inc. (Utica, N.Y.) and the Ti-Screw Suture Anchors by Zimmer Biomet (Warsaw, Ind.). FIGS. 1A and 1B depict a prior art metal anchor 100 of typical construction having a threaded distal portion and a proximal drive portion with a proximally positioned eyelet through which suture is passed. Skilled artisans will agree that it is not possible to produce the anchor of FIGS. 1A and 1B with a central lumen. If a biodegradable alloy were to be substituted for the standard alloy from which anchor 100 is currently constructed, the anchor would dissolve in the manner taught by Janko, that is, from the external surfaces inward. Absorption of the anchor in this manner allows portions of the anchor to remain in the body well past the time at which the anchor has the ability to function effectively to maintain tissue in contact with bone, and may allow first portions of the anchor to become detached from a second portion of the anchor that remains secured in the bone so as to create loose bodies in the region, a negative effect that can have very serious consequences.

Accordingly there remains a pressing need in the art for a metallic bioresorbable tissue anchoring implant configured such that all portions of the implant degrade over a short predetermined period of time while maintaining it tissue anchoring capability and preventing the generation of loose bodies therefrom.

SUMMARY OF THE PRESENT INVENTION

Through thorough analysis of the presently available options, the inventors have discovered that it is possible to construct a suture anchoring implant device from a bioresorbable alloy wherein the device is totally absorbed in a short predetermined period of time in a manner which preserves the pull-out strength and will not generate loose bodies.

Accordingly, it is an objective of the present invention to provide a suture anchoring implant device for affixing a soft tissue graft to a prepared socket in a boney surface, wherein the device is of a generally tubular construction, with a proximal end and a distal end, further wherein the device:

(a) has an outer surface provided with a plurality of integral threads;
(b) has an inner surface defining a central lumen that extends from the proximal to the distal end of the device, wherein the proximal portion of the central lumen is provided with integral torque-receiving features that allow the transmission of torque to the implant necessary to drive the device into the prepared socket; and
(c) is formed from a bioresorbable metallic alloy.

In the context of the present invention, each of the plurality of integral threads on the outer surface has a height defined the major diameter of the thread less the minor diameter of the thread and a width defined as the measurement across the thread at half the height of said thread. In one embodiment, all the threads have substantially the same height. Alternatively, the thread height may taper from the proximal to distal end. In preferred embodiments, the ratio of thread width to thread height is greater that 0.3, more preferably greater than 0.5, more preferably greater than 0.7.

In the context of the present invention, the bioresorbable metallic alloy is preferably a magnesium-based, iron-based or zinc-based alloy. The device may optionally include one or more bioactive therapeutic agent, for example in the form of a surface coating or incorporated into device itself (e.g., into the pores of the bioresorbable metallic alloy from which the device is formed). Illustrative bioactive therapeutic agent include, but are not limited to, peptides, nucleic acids, hormones, chemical drugs, or other biological agents, useful for enhancing the healing process.

It is another objective of the present invention to configure the implant device such that the proximal portion is absorbed first so as to maintain the requisite structural integrity during healing and prevent the generation of loose foreign bodies. In one embodiment, this objective is characterized by the use of a stepped central lumen, wherein the interior diameter of the proximal portion is designed to be greater than the diameter of the distal portion. In another embodiment, the cross-sectional area of the proximal portion of said central lumen is designed to greater than the cross-sectional area of the distal portion of said central lumen. In yet another embodiment, the cross-section of distal portion of the device is designed to be heavier than the cross-section of proximal portion of the device.

It is yet a further objective of the present invention to provide a mechanism for securing the suture, for example through the inclusion of a laterally extending suture-retaining member positioned across said central lumen, more preferably positioned within the distal portion of said central lumen.

These and other objects are accomplished in the invention herein described, directed to engineered bioresorbable metal suture anchoring implant devices and systems for their placement in a target boney surface to secure a soft tissue graft thereto. Further objects and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention. In particular, while the invention is described herein with reference to a number of specific embodiments, it will be appreciated that the description is illustrative of the invention and is not constructed as limiting of the invention.

BRIEF DESCRIPTION OF THE DRAWINGS

Various aspects and applications of the present invention will become apparent to the skilled artisan upon consideration of the brief description of figures and the detailed description of the present invention and its preferred embodiments that follows.

DETAILED DESCRIPTION OF THE PREFERRED EMBODIMENTS

Figure 1B:
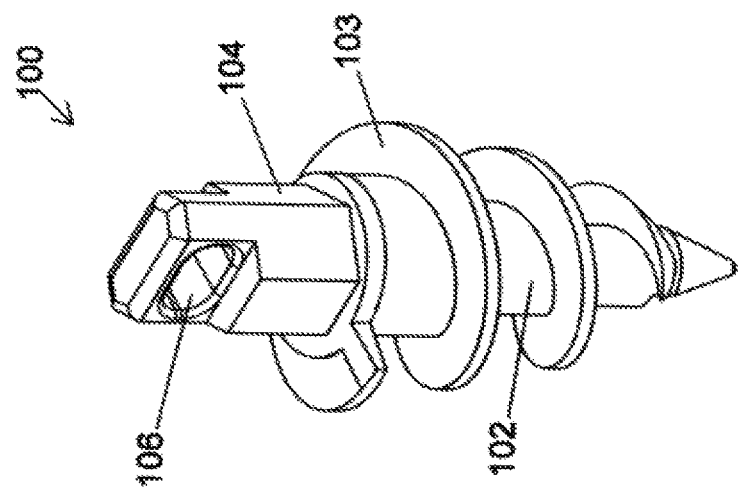
FIG. 1B is a perspective view of the prior art anchor of FIG. 1.

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims. Accordingly, unless otherwise defined, all technical and scientific terms used herein have the same meaning as commonly understood by one of ordinary skill in the art to which the present invention belongs. However, in case of conflict, the present specification, including definitions below, will control.

In the context of the present invention, the following definitions apply:

The words "a", "an" and "the" as used herein mean "at least one" unless otherwise specifically indicated. Thus, for example, reference to an "opening" is a reference to one or more openings and equivalents thereof known to those skilled in the art, and so forth.

The term "proximal" as used herein refers to that end or portion which is situated closest to the user of the device, farthest away from the target surgical site. In the context of the present invention, the proximal end of the anchoring implant of the present invention includes the integral torque-receiving features designed to interact with a suitable torque-transmitting insertion device, such as an implant driver, and thereby allow the transmission of torque to the implant necessary to drive the implant into the prepared socket.

The term "distal" as used herein refers to that end or portion situated farthest away from the user of the device, closest to the target surgical site. In the context of the present invention, the distal end of the anchoring implant of the present invention includes components adapted to fit within the pre-formed implant-receiving socket.

In the context of the present invention, the terms "cannula" and "cannulated" are used to generically refer to the family of rigid or flexible, typically elongate lumened surgical instruments that facilitate access across tissue to an internally located surgery site.

The terms "tube" and "tubular" are interchangeably used herein to refer to a generally round, long, hollow component having at least one central opening often referred to as a "lumen".

The terms "lengthwise" and "axial" as used interchangeably herein to refer to the direction relating to or parallel with the longitudinal axis of a device. The term "transverse" as used herein refers to the direction lying or extending across or perpendicular to the longitudinal axis of a device.

The term "lateral" pertains to the side and, as used herein, refers to motion, movement, or materials that are situated at, proceeding from, or directed to a side of a device.

The term "medial" pertains to the middle, and as used herein, refers to motion, movement or materials that are situated in the middle, in particular situated near the median plane or the midline of the device or subset component thereof.

As discussed above, when a tissue, more particularly a soft connective tissue in a joint space, becomes damaged or torn from its associated bone or cartilage, surgery is usually required to reattach the tissue or reconstruct the bone. The present invention is directed to various means and mechanisms for securing the displaced tissue to the boney tissue associated therewith.

As used herein, the term "tissue" refers to biological tissues, generally defined as a collection of interconnected cells that perform a similar function within an organism. Four basic types of tissue are found in the bodies of all animals, including the human body and lower multicellular organisms such as insects, including epithelium, connective tissue, muscle tissue, and nervous tissue. These tissues make up all the organs, structures and other body contents. While the present invention is not restricted to any particular soft tissue, aspects of the present invention find particular utility in the repair of connective tissues such as ligaments or tendons, particularly those of the shoulder, elbow, knee or ankle joint.

In a similar fashion, while the present invention is not restricted to any particular boney tissue, a term used herein to refer to both bones and cartilage, aspects of the present invention find particular utility in the repair or reattachment of connective tissues to the boney elements of the shoulder, elbow, knee or ankle joint.

When the damaged tissue is of sufficient quantity and quality, the damaged portion may simply be directly reattached to the bone from which it was torn so that healing back to the bone can take place. However, in other situations, a "graft" may be needed to stimulate regrowth and permanent attachment. In the context of the present invention, the term "graft" refers to any biological or artificial tissue being attached to the boney tissue of interest, including:

Autografts, i.e., grafts taken from one part of the body of an individual and transplanted onto another site in the same individual, e.g., ligament graft;

Isografts, i.e., grafts taken from one individual and placed on another individual of the same genetic constitution, e.g., grafts between identical twins;

Allografts, i.e., grafts taken from one individual placed on genetically non-identical member of the same species; and Xenografs, i.e., grafts taken from one individual placed on an individual belonging to another species, e.g., animal to man.

Autografts and isografts are usually not considered as foreign and, therefore, do not elicit rejection. Allografts and xenografts are recognized as foreign by the recipient thus carry a high risk of rejection. For this reason, autographs and isografts are most preferred in the context of the present invention.

Surgical interventions such as contemplated herein generally require the boney tissue to be prepared for receiving the graft. In the context of the present invention, such preparation includes the formation of a "socket", i.e., a hole punched or drilled into the bone into which a prosthetic device such as an implant may be received. The socket may be prepared at the desired target location using conventional instruments such as drills, taps, punches or equivalent hole-producing devices.

In the context of the present invention, the suture-anchoring implant is fabricated from a "bioresorbable" (also referred to as "biodegradable" and "bioabsorbable") material, more particularly a bioresorbable metal designed to degrade safely within the body. Examples of such bioresorbable metals include, but are not limited to magnesium-based, iron-based and zinc-based alloys. Further examples of suitable bioresorbable metals are described by in U.S. Pat.

Nos. 8,591,672 and 8,246,762 to Janko et al., the contents of which are hereby incorporated by reference in their entirety.

As discussed in Janko, in certain embodiments, the anchoring implant may further include a bioactive therapeutic agent (e.g., drugs), either in the form of a surface coating or incorporated into the body of the implant (e.g., into the pores of the alloy from which the implant was made, into a recess in the surface of the device, or in a passageway through the device). In certain embodiments, the implantable medical device further comprises a biodegradable gel. In yet further embodiments, a biodegradable gel may be coated upon the surface of the implant or incorporated into the body of the implant (e.g., into the pores of the alloy from which the implant was made, into a recess in the surface of the device, or in a passageway through the device). In certain embodiments, the biodegradable gel includes the above-noted bioactive therapeutic agent, examples of which, include but are not limited to, peptides, nucleic acids, hormones, chemical drugs, or other biological agents, useful for enhancing the healing process.

While certain procedures contemplate directly attaching the graft to the bone, the more common route involves the employment of an implant specially configured to hold and/or enable attachment of the graft to the boney tissue. As used herein, the terms "implant" and "anchor" are used interchangeably to refer to a prosthetic device fabricated from a biocompatible and/or inert material. In the context of the present invention, examples of such "anchoring implants" include conventional as well as knotless anchors (such as described in co-pending U.S. patent application Ser. No. 14/636,389 filed Mar. 3, 2015, the entire contents of which are hereby incorporated by reference herein), both of the screw-threaded and interference variety.

In the context of the present invention, the proximal end of the anchoring implant is provided with torque-receiving features, preferably integral to the device, that are designed to interact with a suitable torque-transmitting insertion device, such as an implant driver, and thereby allow transmission of the requisite amount of torque needed to drive the implant into the prepared socket. Hereinbelow, the present invention makes reference to various lock-and-key type mating mechanisms that serve to establish and secure the axial and rotational arrangement between the anchor and the driver. For example, the torque torque-receiving feature characterizing the proximal end of the anchor may be a polygonal recess while the torque-transmitting feature characterizing the distal end of the driver is a complementary polygonal head (such as found on the conventional hex key or "Allen" key). In another embodiment, the proximal end includes one or more axially extending slots while the driver is a slotted, flat blade or crosshead ("Phillips head") screwdriver. However, other embodiments will be readily apparent to the skilled artisan. Moreover, it will be readily understood by the skilled artisan that the position of the respective coordinating elements (e.g., recessed slots and grooves that mate with assorted projecting protrusions, protuberances, tabs and splines) may be exchanged and/or reversed as needed.

The present invention makes reference to insertion devices commonly referred to in the art as "drills" and "drivers", i.e., devices that "drill" the socket and "drive" the implant into the socket. In the context of the present invention, the drills and drivers may be conventional, e.g., rigidly linear as previously herein described, or, as discussed in detail herein, "off-axis", e.g., having an angularly offset distal portion adapted to drill off-axis sockets in boney tissues that are remote and difficult to access and drive therein the corresponding implant, such as the anchoring implant of the present invention.

The present invention contemplates securing the graft to the implant via sutures. In the context of the present invention, the term "suture" refers to a thread-like strand or fiber used to hold body tissues after surgery. Sutures of different shapes, sizes, and thread materials are known in the art and the present invention is not restricted to any particular suture type. Accordingly, in the context of the present invention, the suture may be natural or synthetic, monofilament or multifilament, braided or woven, permanent or resorbable, without departing from the spirit of the invention.

The instant invention has both human medical and veterinary applications. Accordingly, the terms "subject" and "patient" are used interchangeably herein to refer to the person or animal being treated or examined. Exemplary animals include house pets, farm animals, and zoo animals. In a preferred embodiment, the subject is a mammal, more preferably a human.

Hereinafter, the present invention is described in more detail by reference to the Figures and Examples. However, the following materials, methods, figures, and examples only illustrate aspects of the invention and are in no way intended to limit the scope of the present invention. For example, while the present invention makes specific reference to arthroscopic procedures, it is readily apparent that the teachings of the present invention may be applied to other minimally invasive procedures and are not limited to arthroscopic uses alone. As such, methods and materials similar or equivalent to those described herein can be used in the practice or testing of the present invention.

EXAMPLES

Figure 1A:
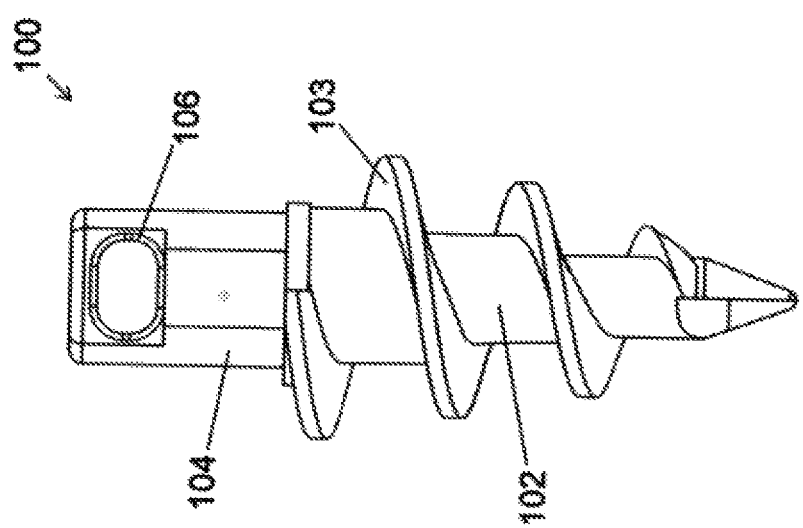
FIG. 1A is a side elevational view of a prior art metal anchor.

FIGS. 1A and 1B depict a prior art metal anchor 100 of typical construction having a threaded distal portion and a proximal drive portion with a proximally positioned eyelet through which suture is passed. Specifically, prior art anchor 100 has a threaded distal portion 102 with threads 103 and a proximal drive portion 104 in which is formed eyelet 106 through which suture is passed. In use, sutures (generally two or three) are loaded into anchor 100 by passing the sutures through eyelet 106. The anchor is threaded into a socket formed in the bone with the proximal (top) end of the implant recessed below the bone surface. One leg of each suture is passed through the tissue graft and the tissue is secured to the bone by tying knots in the suture leg pairs. Anchor 100 remains in the bone and, since it does not degrade, retains its tissue retaining function through the healing process and beyond.

Figure 2C:
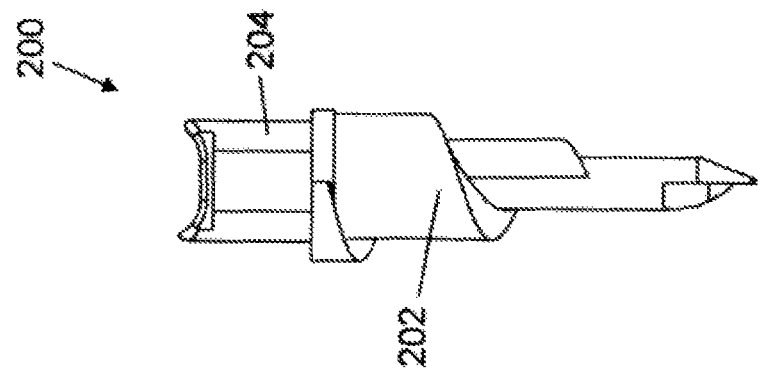
FIG. 2C is a side elevational view of the anchor of FIG. 2A with 0.01 inches (0.25 mm) of erosion from all external surfaces.
Figure 2B:
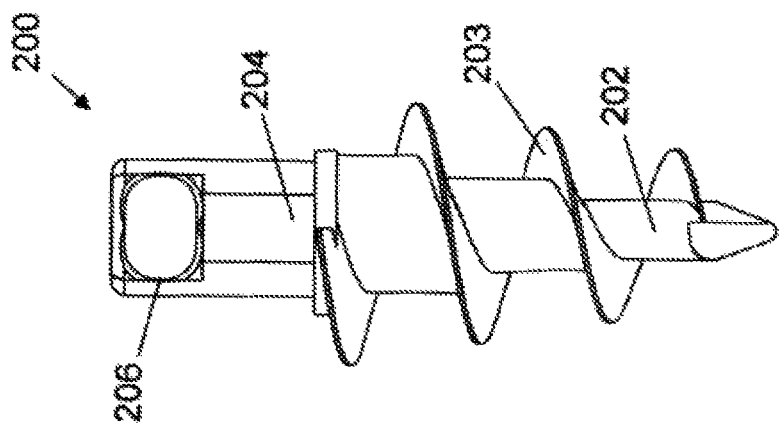
FIG. 2B is a side elevational view of the anchor of FIG. 2A with 0.005 inches (0.12 mm) of erosion from all external surfaces.
Figure 2A:
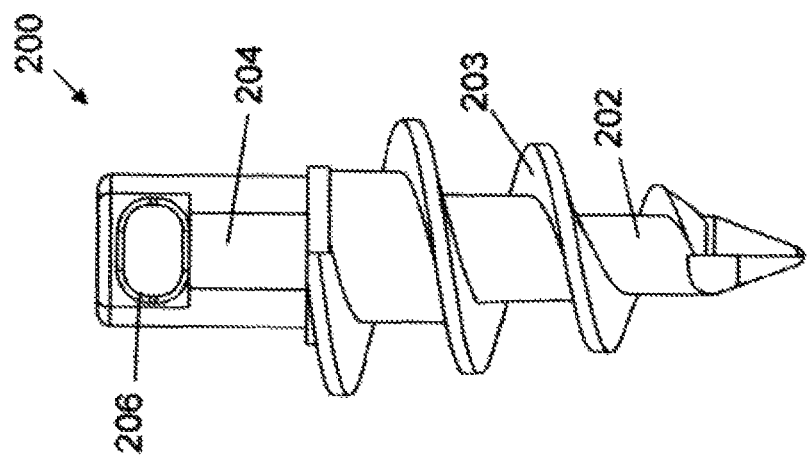
FIG. 2A is a side elevational view of an anchor with the geometric configuration of the anchor of FIG. 1A but constructed from a bioresorbable alloy.

FIGS. 2A through 2C depict anchor 200 that is geometrically identical to anchor 100 but constructed of a biodegradable alloy as taught by Janko in U.S. Pat. Nos. 8,591,672 and 8,246,762. FIG. 2A depicts anchor 200 as placed in the bone and with distal portion 202, proximal drive portion 204, eyelet 206 and tapering threads 203. FIGS. 2B and 2C depict material being progressively dissolved (or more precisely "degraded" or "resorbed") as taught by Janko. As depicted in FIG. 2B, anchor 200 has lost 0.005 inches (0.12 mm) from all exposed surfaces by dissolution or resorption. Note that threads 203 have decreased in thickness and the thickness of proximal and lateral walls of eyelet 206 have decreased significantly as well. In FIG. 2C, anchor 200 has lost 0.01 inches (0.25 mm) from all exposed surfaces by dissolution. The proximal and lateral walls of eyelet 206 have been totally resorbed along with threads 203 of threaded distal portion 202. A significant portion of distal portion 202 and proximal drive portion 204 remains; however, there is no longer a functioning eyelet 206, and remaining artifacts of the lateral walls of the eyelet are protruding and may cause irritation of the tissue graft in close proximity. Also, with threads 203 resorbed from distal portion 202, no feature on anchor 200 retains anchor 200 in the bone so it is possible that the partially resorbed artifact of anchor 200 as depicted in FIG. 2C could become dislodged and become a loose body in the joint space.

FIGS. 3A through 3D depict anchor 400 formed in accordance with the principles of the instant invention from a bioresorbable metal alloy. Anchor 400 is of tubular form and has an external surface 420 with threads 422, a coaxial central lumen 430 having proximal end features 432 configured for coupling to a torsional drive element and a distal end 444. Proximal portion 436 of lumen 430 is of diameter 438; distal portion 440 of lumen 430 is of diameter 441, diameter 441 being less than diameter 438. Positioned distance 442 from distal most surface 444 of anchor 400, transversely extending member 446 of thickness 448 with a rounded distal end is centrally positioned within distal portion 440 of lumen 430. In use, one or more sutures are loaded into implant 400 prior to placement of anchor 400 into a prepared socket in a boney surface. The sutures enter and leave anchor 400 via proximal end 436 of lumen 430, the mid-portions of the sutures being wrapped around the rounded distal end of transversely extending member 446 such that the sutures may slide freely when securing a tissue graft using the sutures.

FIGS. 4A through 4D depict anchor 400 from FIG. 3A-3D with 0.005 inches (0.12 mm) removed from all exposed surfaces such as typically occurs during resorption of the anchor after placement in bone at a first time after placement. Material is removed from external surface 420 and threads 422, from proximal portion 436 and distal portion 440 of lumen 430, and from transversely extending member 446. Diameter 438 of proximal portion 436 of lumen 430 and diameter 441 of distal portion 440 of lumen 430 are both increased by 0.01 inches (0.25 mm). Thickness 448 of transversely extending member 446 is reduced by 0.01 inches (0.25 mm). Nevertheless, the structural integrity of anchor 400 is maintained. In particular, threads 422 are engaged with the surrounding bone and transversely extending member 446 maintains structural integrity such that anchor 400 continues to anchor tissue connected thereto by sutures.

FIGS. 5A through 5D depict anchor 400 with 0.01 inches (0.25 mm) removed from all exposed surfaces as occurs during resorption of the anchor after placement in bone at a second, later time after placement. Material is removed from external surface 420 and threads 422, from proximal portion 436 and distal portion 440 of lumen 430, and from transversely extending member 446. Diameter 438 of proximal portion 436 of lumen 430 and diameter 441 of distal portion 440 of lumen 430 are increased by 0.02 inches (0.5 mm) from their original values. Thickness 448 of transversely extending member 446 is reduced by 0.02 inches (0.5 mm) from its original value. However, once again, the structural integrity of anchor 400 is maintained. Threads 422 are still engaged with the surrounding bone and transversely extending member 446 maintains structural integrity, though the pull-out strength is significantly reduced. However, resorption of anchor 400 as depicted in FIG. 5A through 5D occurs after significant healing of the soft tissue to the bone has occurred; thus, any reduction in pull-out strength is compensated for by an increase in tissue adhesion. In any event, the structure of anchor 400 with 0.01 inches of tissue biodegraded from all exposed surfaces is still continuous so as to prevent the generation of loose bodies.

FIGS. 6A through 6D depict anchor 400 with 0.015 inches (0.37 mm) removed from all exposed surfaces as occurs during degradation of the anchor after placement in bone at a third time, even later after placement. At this point, resorption of anchor 400 is effectively complete with transversely extending member 446 and all of the tubular walls gone except for a small portion of the threads. However, as resorption of anchor 400 as depicted in FIG. 6A through 6D occurs after complete healing of the soft tissue to the bone has occurred, significant retention is no longer needed.

Figure 3A:
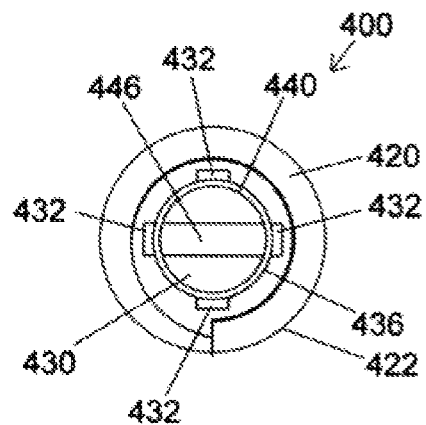
FIG. 3A is a plan view of a suture anchor formed of bioabsorbable alloy and constructed in accordance with the principles of this invention.
Figure 3B:
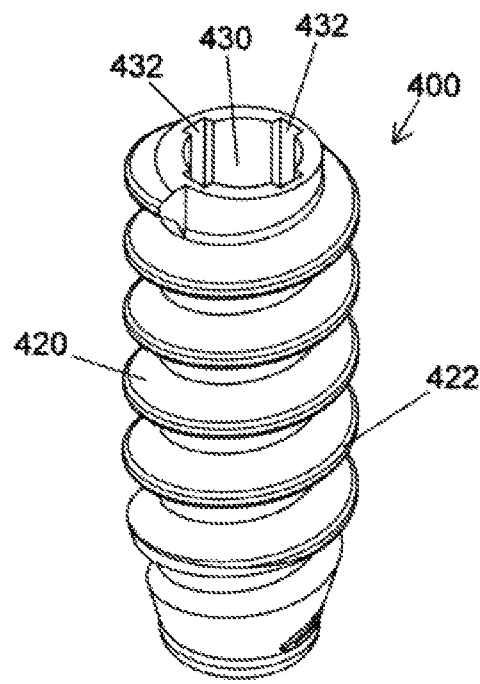
FIG. 3B is a perspective view of the anchor of FIG. 3A.
Figure 3C:
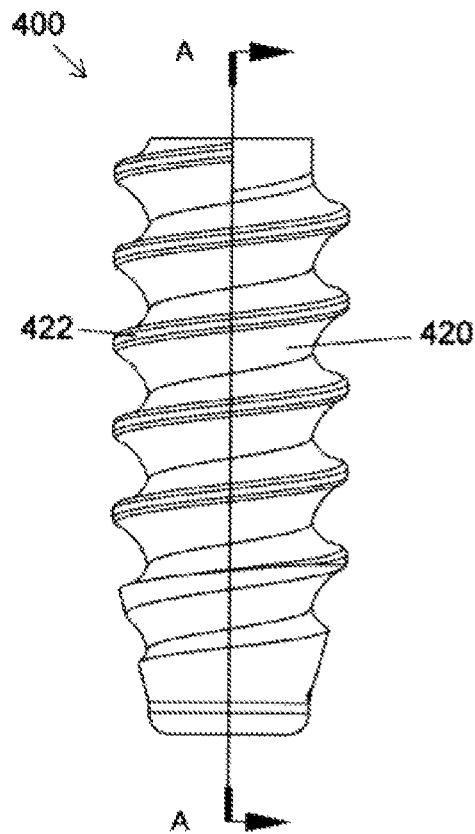
FIG. 3C is a side elevational view of the anchor of FIG. 3A.
Figure 3D:
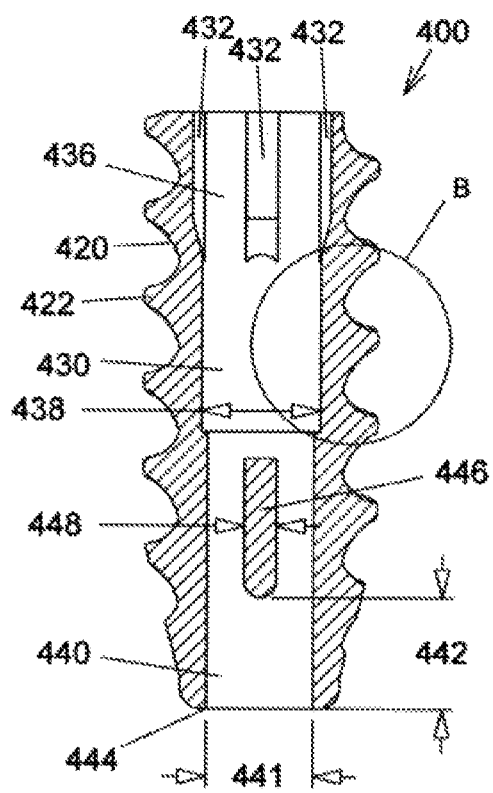
FIG. 3D is a side elevational sectional view of the objects of FIG. 3C at location A-A of FIG. 3C.
Figure 3E:
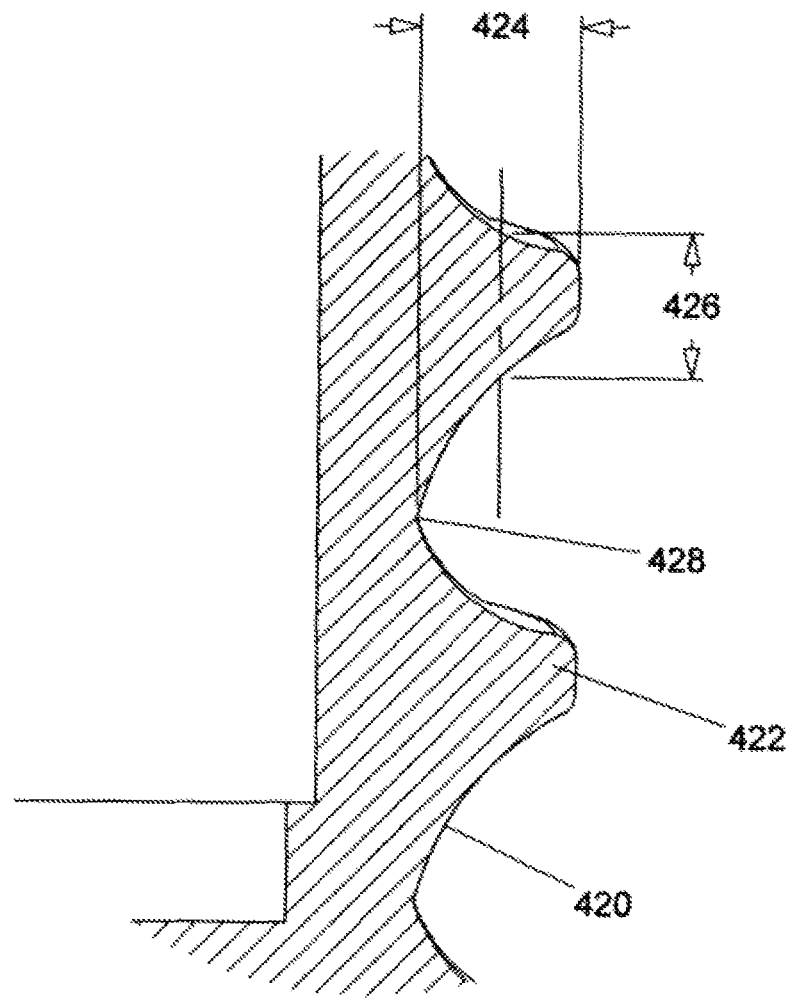
FIG. 3E is an expanded view of the objects of FIG. 3D at location B.
Figure 4A:
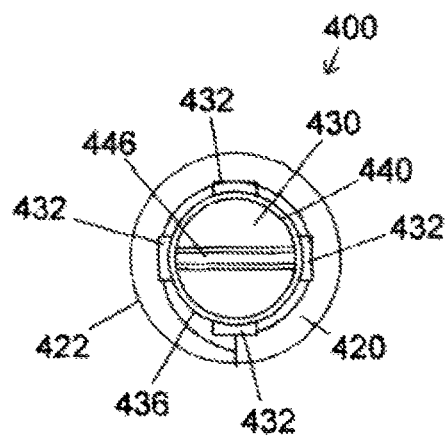
FIG. 4A is a plan view of the anchor of FIG. 3A with 0.005 inches (0.12 mm) removed from all external surfaces.
Figure 4B:
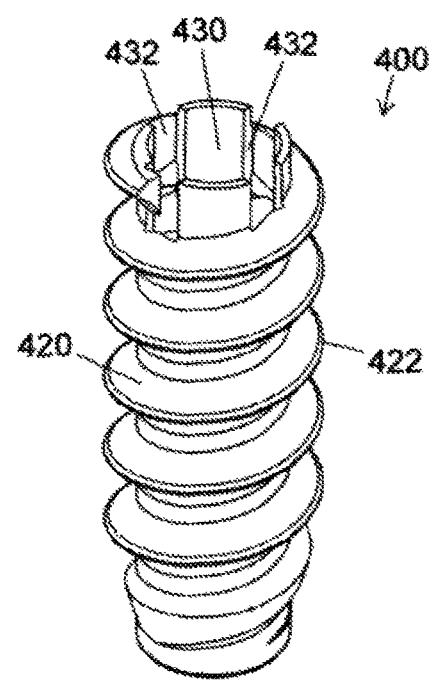
FIG. 4B is a perspective view of the anchor of FIG. 4A.
Figure 4C:
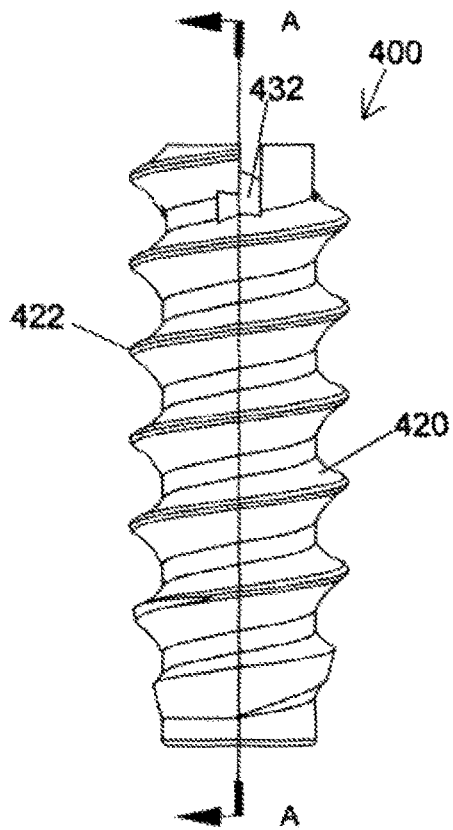
FIG. 4C is a side elevational view of the anchor of FIG. 4A.
Figure 4D:
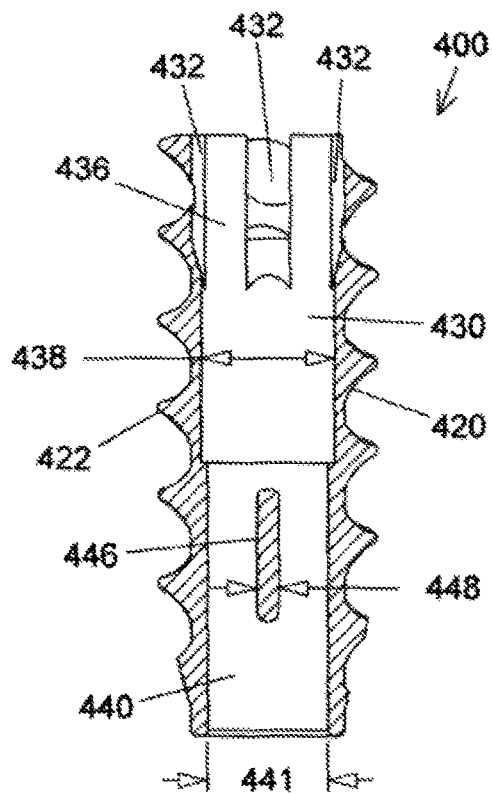
FIG. 4D is a side elevational sectional view of the objects of FIG. 4C at location A-A of FIG. 4C.
Figure 5A:
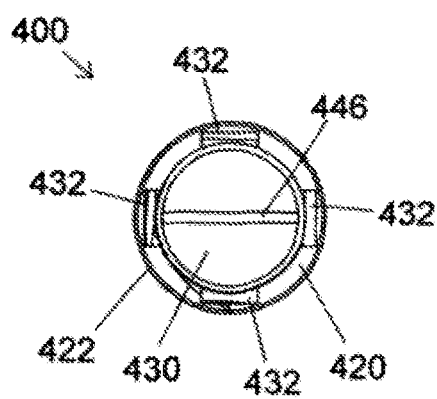
FIG. 5A is a plan view of the anchor of FIG. 3A with 0.01 inches (0.25 mm) removed from all external surfaces.
Figure 5B:
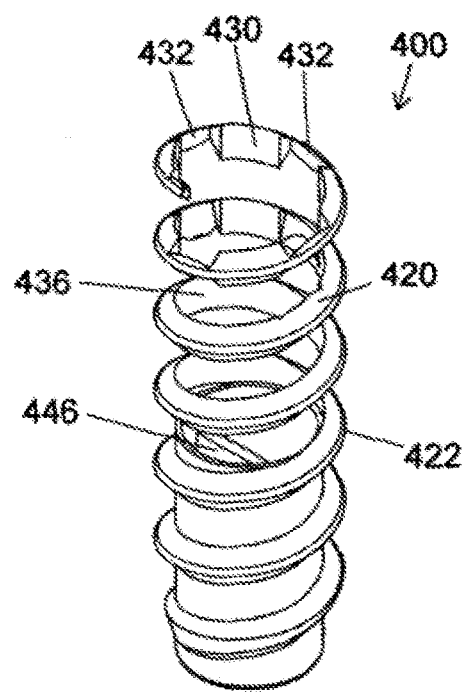
FIG. 5B is a perspective view of the anchor of FIG. 4A.
Figure 5C:
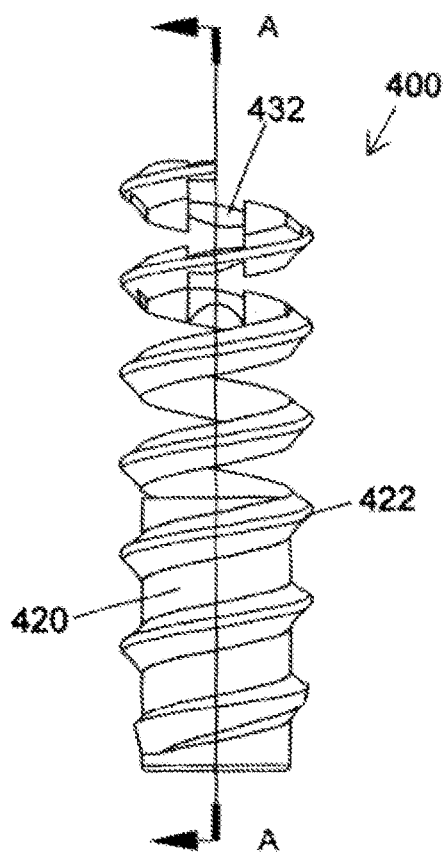
FIG. 5C is a side elevational view of the anchor of FIG. 4A.
Figure 5D:
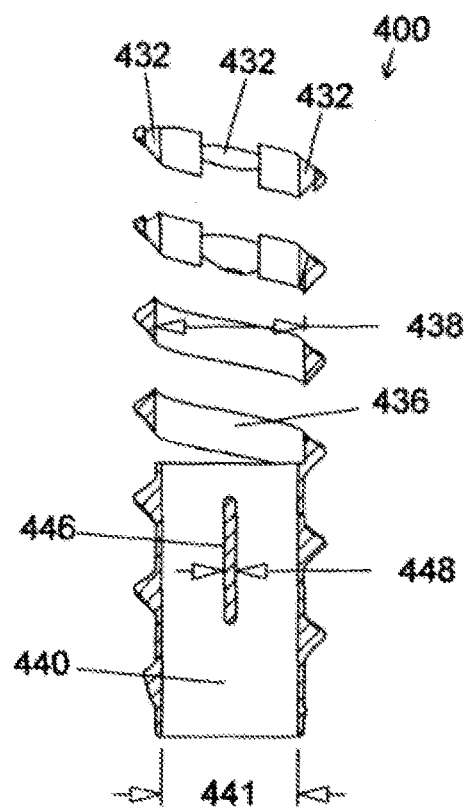
FIG. 5D is a side elevational sectional view of the objects of FIG. 5C at location A-A of FIG. 5C.
Figure 6A:
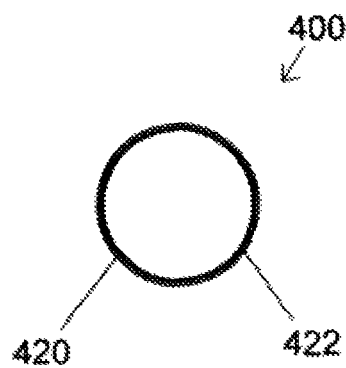
FIG. 6A is a plan view of the anchor of FIG. 3A with 0.015 inches (0.37 mm) removed from all external surfaces.
Figure 6B:
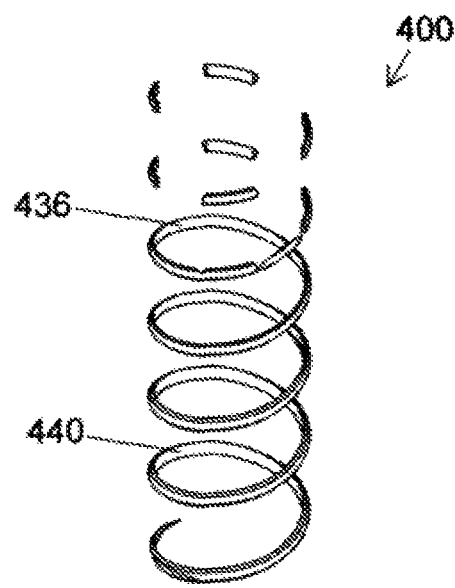
FIG. 6B is a perspective view of the anchor of FIG. 6A.
Figure 6C:
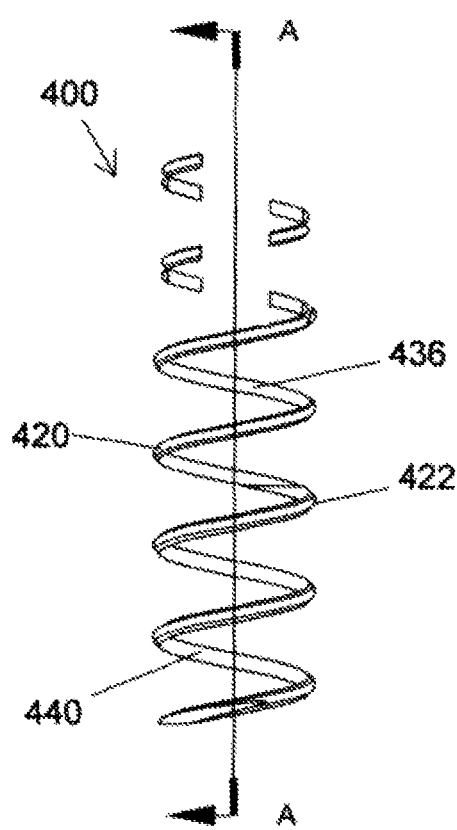
FIG. 6C is a side elevational view of the anchor of FIG. 6A.
Figure 6D:
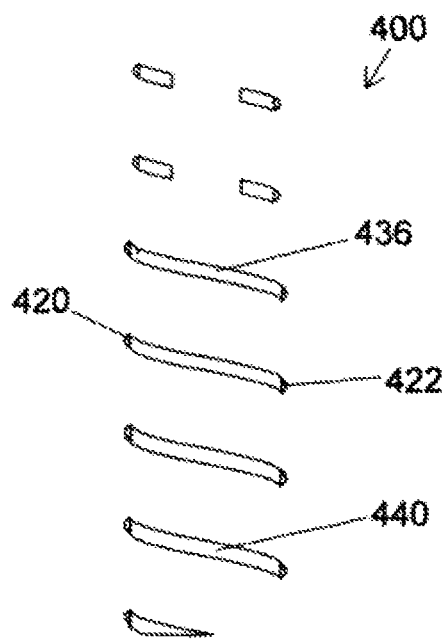
FIG. 6D is a side elevational sectional view of the objects of FIG. 6C at location A-A of FIG. 6C.
Figure 7A:
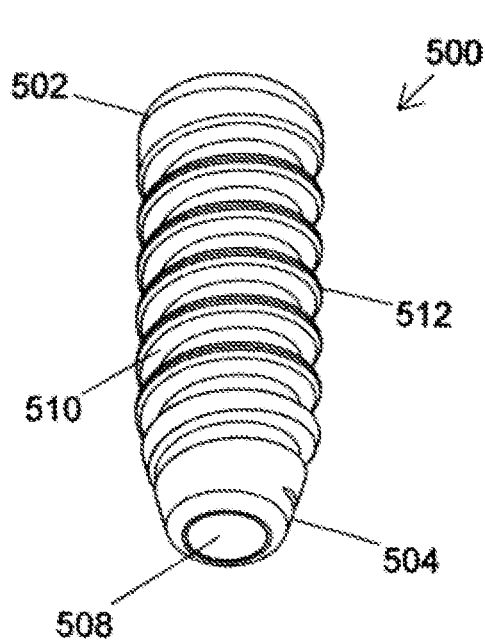
FIG. 7A is a distal perspective view of an interference screw formed of bioabsorbable alloy and constructed in accordance with the principles of this invention.
Figure 7B:
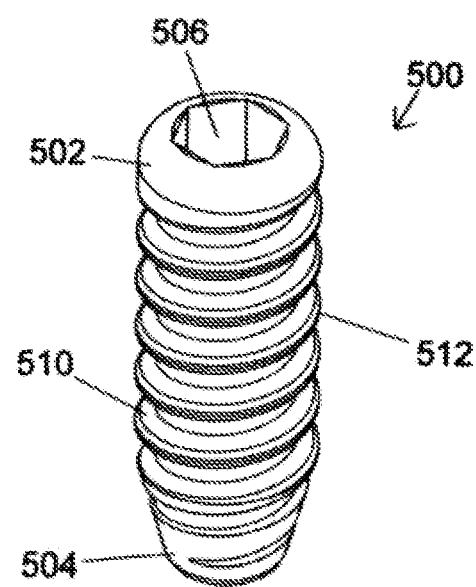
FIG. 7B is a proximal perspective view of the interference screw of FIG. 7A.
Figure 7C:
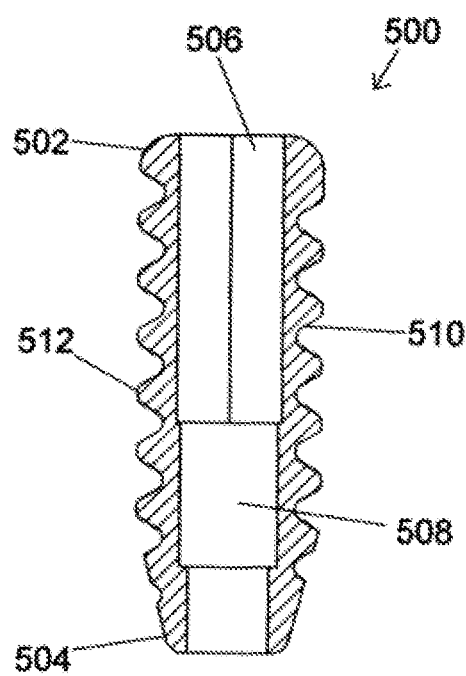
FIG. 7C is a side elevational sectional view of the objects of FIG. 7D at location A-A of FIG. 7D.
Figure 7D:
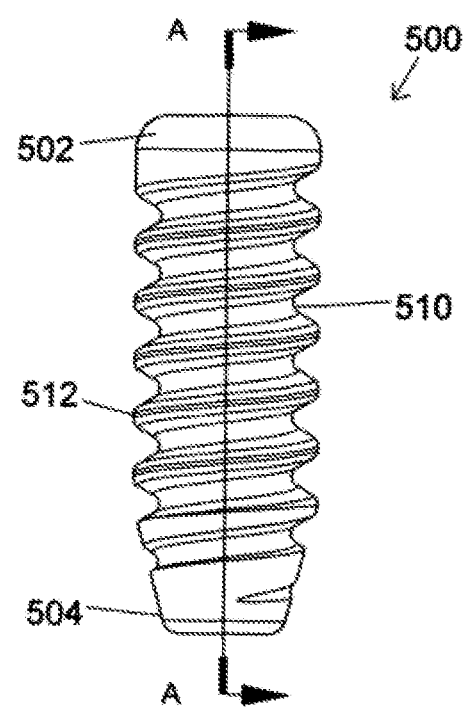
FIG. 7D is a side elevational view of the interference screw of FIG. 7A.

Suture anchors constructed in accordance with the principles of the instant invention maintain structural integrity during the healing process. When healing is complete and anchoring of the tissue to the bone via sutures and the anchor is no longer necessary, the anchor is resorbed in a short predetermined time period in a manner that maintains structural integrity throughout. Because resorption of the anchor begins immediately upon placement in the body, the threads on the anchor are configured to have sufficient material distributed so as to continue to provide resistance to axial displacement as the anchor is resorbed. Referring to FIG. 3E, thread 422 has a thread height 424 and a thread width 426 measured at a distance half of distance 424 from the root 428 of thread 422. The ratio of width 426 to height 424 is preferably greater than 0.3, more preferably greater than 0.5, and still more preferably greater than 0.7. Further, suture anchors of the present invention are configured such that the structural element around which suture is loaded has sufficient material distributed so as to maintain structural strength during resorption of the anchor. When healing has progressed sufficiently resorption of the remainder of the anchor occurs according to a preplanned progression that does not generate loose bodies. The complete absorption of the proximal portions of the implant is accomplished while these portions are connected to the more distal portions since, if the distal portions are dissolved first, the proximal portions may be ejected from the bone socket and become loose bodies. Anchors constructed in accordance with the principles of this invention have distal cross-sections that are heavier than proximal cross-sections to ensure that the proximal cross-sections are absorbed first. The transverse structural element around which suture is loaded is dissolved at a rate which maintains connection between that element and the tubular structure so that it is absorbed at the same time as the tubular structure, or slightly before, again to prevent the generation of loose bodies.

The principles of the instant invention may be advantageously applied to interference screws as well. FIGS. 7A through 7D depict an interference screw 500 of the present invention formed from a bioabsorbable metal alloy. Interference screw 500 has a proximal end 502, a distal end 504, and a central lumen with a hexagonal proximal portion 506 and a distal portion 508. Lumen distal portion 508 of anchor 500 is cylindrical. In other embodiments distal portion 508 may be hexagonal, square, or have other configurations. Lumen distal portion 508 of anchor 500 optionally may have a stepped diameter as depicted or may be tapered, the distal portion being of a smaller diameter than the more proximal portion. Proximal portion 506 may have other configurations that allow the transmission of torque from a driver device to anchor 500. It is required, however, that the cross-section of proximal lumen portion 506 is greater than the cross-section of distal lumen portion 508. Outer surface 510 of anchor 500 has formed thereon threads 512, threads 512 being configured in accordance with the principles of the present invention. That is, threads 512 have a form of sufficient mass and cross-section to ensure that threads 512 retain resistance to axial movement during the resorption of anchor 500. Though the thread form may differ from that of anchor 400 (FIG. 3E) the same preferred ratios of thread width to thread height apply.

INDUSTRIAL APPLICABILITY

As noted previously, there is a need in the art for metallic bioresorbable tissue anchoring implants configured such that all portions of the implant resorb over a short predetermined period of time while maintaining its tissue anchoring capability and preventing the generation of loose bodies therefrom. The present invention addresses this need by providing a suture-anchoring implant formed from a bioresorbable metallic alloy, more particularly a threaded implant of generally tubular construction characterized by a central lumen that extends from the proximal to the distal end of the implant, wherein the cross-section of distal portion of the implant is heavier (i.e., contains more bioresorbable material) than the cross-section of proximal portion of the implant so as to ensure that the proximal cross-sections are absorbed first and thus the generation of loose bodies is substantially prevented. Although described in detail with respect to ligament repairs, such as repair of a torn rotator cuff, it will be readily apparent to the skilled artisan that the utility of the present invention extends to other tissues and injuries.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

The invention has been illustrated by reference to specific examples and preferred embodiments. However, it should be understood that the invention is intended not to be limited by the foregoing description, but to be defined by the appended claims and their equivalents.

What is claimed:

1. A suture anchoring implant device for affixing a soft tissue graft to a prepared socket in a target boney surface, wherein the device has a generally tubular construction, with a proximal portion and proximal end and a distal portion and distal end, further wherein the device:
   (a) has an outer surface provided with a plurality of integral threads, each of which is characterized by a major diameter and a minor diameter, wherein each of said plurality of integral threads has (i) a thread height defined as the difference between its major diameter and its minor diameter and (ii) a thread width defined as the measurement across said thread at half the height of said thread, further wherein each of said plurality of integral threads exhibits a ratio of thread width to thread height that is greater than 0.3;
   (b) has an inner surface defining a central lumen that extends from the proximal to the distal end of the device, wherein the proximal portion of the central lumen is provided with an integral torque-receiving feature that allows the transmission of torque to the device necessary to drive the device into the prepared socket; and
   (c) is formed from a bioresorbable metallic alloy.

2. The suture anchoring implant device of claim 1, wherein the diameter of the central lumen is stepped such that the interior diameter of the proximal portion is greater than the diameter of the distal portion.

3. The suture anchoring implant device of claim 1, wherein the proximal portion of said central lumen exhibits a cross-sectional area that is greater than a cross-sectional area exhibited by the distal portion of said central lumen.

4. The suture anchoring implant device of claim 1, wherein a cross-section taken at the distal portion of the device contains more of said bioresorbable metallic alloy than an equivalent cross-section taken at the proximal portion of the device, thereby ensuring that proximal cross-sections are absorbed first and the generation of loose bodies is prevented.

5. The suture anchoring implant device of claim 1, wherein the device further includes a laterally extending suture-retaining member positioned across said central lumen.

6. The suture anchoring implant device of claim 5, wherein said laterally extending suture-retaining member is within the distal portion of said central lumen.

7. The suture anchoring implant device of claim 1, wherein the respective heights of each of said plurality of integral threads is substantially identical.

8. The suture anchoring implant device of claim 1, wherein the respective heights of each of said plurality of integral threads taper from proximal to distal end.

9. The suture anchoring implant device of claim 1, wherein each of said plurality of integral threads exhibits a ratio of thread width to thread height that is greater than 0.5.

10. The suture anchoring implant device of claim 9, wherein each of said plurality of integral threads exhibits a ratio of thread width to thread height that is greater than greater than 0.7.

11. The suture anchoring implant device of claim 10, wherein said integral torque-receiving feature is a polygonal recess.

12. The suture anchoring implant device of claim 1, wherein said integral torque-receiving feature is one or more axially extending slots.

13. The suture anchoring implant device of claim 1, wherein bioresorbable metallic alloy is selected from the group consisting of magnesium-based, iron-based and zinc-based alloys.

14. The suture anchoring implant device of claim 1, wherein the device further includes a bioactive therapeutic agent.

15. The suture anchoring implant device of claim 14, wherein said bioactive therapeutic agent is in the form of a surface coating.

16. The suture anchoring implant device of claim 14, wherein said bioactive therapeutic agent is incorporated into pores of the bioresorbable metallic alloy from which the device is formed.

17. The suture anchoring implant device of claim 14, wherein said bioactive therapeutic agent is selected from the group consisting of peptides, nucleic acids, hormones, chemical drugs, or other biological agents, useful for enhancing the healing process.

* * * * *